United States Patent
Al-Ali

(10) Patent No.: US 10,939,831 B2
(45) Date of Patent: Mar. 9, 2021

(54) PRESSURE-SENSING BLEED-BACK CONTROL VALVE WITH IMPROVED SEALING

(71) Applicant: Firas Al-Ali, Hudson, OH (US)

(72) Inventor: Firas Al-Ali, Hudson, OH (US)

(73) Assignee: CYGNUS MEDICAL, LLC, Akron, OH (US)

( * ) Notice: Subject to any disclaimer, the term of this patent is extended or adjusted under 35 U.S.C. 154(b) by 446 days.

(21) Appl. No.: 15/907,429

(22) Filed: Feb. 28, 2018

(65) Prior Publication Data

US 2018/0184912 A1 Jul. 5, 2018

Related U.S. Application Data

(63) Continuation-in-part of application No. 15/782,664, filed on Oct. 12, 2017, now Pat. No. 10,625,067.
(Continued)

(51) Int. Cl.
| | |
|---|---|
| *A61B 5/0215* | (2006.01) |
| *A61B 5/00* | (2006.01) |
| *A61M 39/24* | (2006.01) |
| *A61M 39/06* | (2006.01) |
| *A61M 39/22* | (2006.01) |

(52) U.S. Cl.
CPC .......... *A61B 5/0215* (2013.01); *A61B 5/6851* (2013.01); *A61B 5/6852* (2013.01); *A61M 39/06* (2013.01); *A61M 39/24* (2013.01); *A61M 2039/062* (2013.01); *A61M 2039/0666* (2013.01); *A61M 2039/0686* (2013.01); *A61M 2039/226* (2013.01); *A61M 2039/229* (2013.01); *A61M 2039/2406* (2013.01)

(58) Field of Classification Search
CPC ... A61B 5/0215; A61B 5/6851; A61B 5/6852; A61M 39/06; A61M 39/24
USPC .......................................... 604/537
See application file for complete search history.

(56) References Cited

U.S. PATENT DOCUMENTS

| | | | |
|---|---|---|---|
| 3,865,100 A | 2/1975 | Kanai et al. | |
| 4,160,448 A | 7/1979 | Jackson | |
| (Continued) | | | |

FOREIGN PATENT DOCUMENTS

| | | |
|---|---|---|
| CA | 2682474 A1 | 7/2008 |
| CA | 2974544 A1 | 12/2016 |
| (Continued) | | |

OTHER PUBLICATIONS

Vascular Solutions, Guardian II Hemostasis Vavle, brochure or product literature, (2014).
(Continued)

*Primary Examiner* — Bhisma Mehta
*Assistant Examiner* — Nidah M Hussain
(74) *Attorney, Agent, or Firm* — Dominic A. Frisina

(57) ABSTRACT

A hemostasis or bleed-back control valve such as a Tuohy-Borst adapter is provided that is capable of sensing pressure in vivo. The valve may include a main valve body having a lumen. An upstream main seal may be disposed in the lumen of the main valve body. A catheter fitting may be disposed at a downstream end of the main valve body. A pressure transducer may be in fluid communication with the lumen of the main valve body. Such devices may be suitable for exploratory or interventional medicine involving catheterization.

20 Claims, 11 Drawing Sheets

Related U.S. Application Data

(60) Provisional application No. 62/407,258, filed on Oct. 12, 2016.

(56) References Cited

U.S. PATENT DOCUMENTS

| | | | |
|---|---|---|---|
| 4,407,298 A | 10/1983 | Lentz et al. | |
| 4,545,389 A | 10/1985 | Schaberg et al. | |
| 4,587,975 A | 5/1986 | Salo et al. | |
| 4,842,591 A | 6/1989 | Luther | |
| 5,256,149 A | 10/1993 | Banik et al. | |
| 5,334,160 A | 8/1994 | Ellis | |
| 5,342,315 A | 8/1994 | Rowe et al. | |
| 5,358,490 A | 10/1994 | Henry et al. | |
| 5,383,896 A | 1/1995 | Gershony et al. | |
| 5,626,601 A | 5/1997 | Gershony et al. | |
| 5,868,778 A | 2/1999 | Gershony et al. | |
| 5,911,710 A | 6/1999 | Barry et al. | |
| 5,951,583 A | 9/1999 | Jensen et al. | |
| 5,957,952 A | 9/1999 | Gershony et al. | |
| 6,017,359 A | 1/2000 | Gershony et al. | |
| 6,033,366 A | 3/2000 | Brockway et al. | |
| 6,083,207 A | 7/2000 | Heck | |
| 6,287,280 B1 | 9/2001 | Lampropoulos et al. | |
| 6,296,658 B1 | 10/2001 | Gershony et al. | |
| 6,331,176 B1 | 12/2001 | Becker et al. | |
| 6,379,308 B1 | 4/2002 | Brockway et al. | |
| 6,488,674 B2 | 12/2002 | Becker et al. | |
| 6,511,434 B1 | 1/2003 | Haytman et al. | |
| 6,575,960 B2 | 6/2003 | Becker et al. | |
| 6,695,820 B1 | 2/2004 | Armstrong et al. | |
| 6,709,418 B1 | 3/2004 | Aboul-Hosn et al. | |
| 6,896,002 B2 | 5/2005 | Hart et al. | |
| 7,025,727 B2 | 4/2006 | Brockway et al. | |
| 7,347,822 B2 | 3/2008 | Brockway et al. | |
| 7,938,809 B2 | 5/2011 | Lampropoulos | |
| 7,976,503 B2 | 7/2011 | Khan et al. | |
| 8,048,032 B2 | 11/2011 | Root et al. | |
| 8,142,413 B2 | 3/2012 | Root et al. | |
| 8,246,585 B2 | 8/2012 | Schennib | |
| 8,292,850 B2 | 10/2012 | Root et al. | |
| 8,852,147 B2 | 10/2014 | Callan et al. | |
| RE45,380 E | 2/2015 | Root et al. | |
| RE45,760 E | 10/2015 | Root et al. | |
| RE45,776 E | 10/2015 | Root et al. | |
| RE46,116 E | 8/2016 | Root et al. | |
| 9,675,792 B2 | 6/2017 | Bramwell et al. | |
| 9,895,524 B2 | 2/2018 | Lareau | |
| 2002/0010436 A1* | 1/2002 | Becker | A61M 39/06 604/256 |
| 2004/0243044 A1 | 12/2004 | Penegor et al. | |
| 2007/0038143 A1 | 2/2007 | Christensen et al. | |
| 2007/0260219 A1 | 11/2007 | Root et al. | |
| 2008/0171988 A1* | 7/2008 | Blanco | A61B 17/3462 604/167.03 |
| 2008/0243081 A1* | 10/2008 | Nance | A61B 17/3439 604/164.03 |
| 2009/0204078 A1 | 8/2009 | Mitchell et al. | |
| 2009/0318881 A1 | 12/2009 | Shennib | |
| 2010/0324567 A1 | 12/2010 | Root et al. | |
| 2012/0165756 A1 | 6/2012 | Root et al. | |
| 2016/0066932 A1 | 3/2016 | Root et al. | |
| 2016/0346515 A1 | 12/2016 | Buller et al. | |
| 2017/0050003 A1 | 2/2017 | Root et al. | |
| 2018/0064453 A1* | 3/2018 | Garrison | A61M 25/0108 |

FOREIGN PATENT DOCUMENTS

| | | |
|---|---|---|
| WO | 2016040579 A1 | 3/2016 |
| WO | 2016191415 A1 | 12/2016 |

OTHER PUBLICATIONS

Elcam Medical, Sense-IT (DIPT) Disposable Integrated Pressure Transducer . . . , brochure or product literature, (2013).

Elcam Medical, Y-Click, brochure or product literature, (2012).

Sense-IT (DIPT). Product Literature (PDF) [online]. Elcam Medical, Oct. 2018 [retrieved on Jul. 14, 2020]. Unique identification No. <REV-7 Oct. 2018 ISO 13485>. Retrieved from the Internet: <URL: https://www.elcam-medical.com/sites/elcam/UserContent/files/Sense-IT_DIPT_ENG_REV7_10-2018.pdf>.

Y-Click. Product Literature (PDF) [online]. Elcam Medical, Oct. 2018 [retrieved on Jul. 14, 2020]. Unique identification No. <REV-6 Oct. 2018 ISO 13485>. Retrieved from the Internet: <URL: https://www.elcam-medical.com/sites/elcam/UserContent/files/Y-Click_REV6_10-2018_v4.pdf>.

Guardian II Hemostasis Valve. Product Brochure (PDF) [online]. Vascular Solutions, Inc., Sep. 2019 [retrieved on Jul. 14, 2020]. Unique identification No. <MC-005917 Rev>. Retrieved from the Internet: <URL: https://www.teleflex.com/usa/en/product-areas/interventional/coronary-interventions/guardian-ii-hemostasis-valve/Guardian-Hemostasis-Valve-Brochure_MC-005917-r0.pdf>.

SafeSheath Sealing Adapter. Product Sheet (PDF) [online]. Pressure Products Medical Supplies, Inc. [retrieved on Jul. 14, 2020]. Retrieved from the Internet: <URL: http://www.pressure-products.com/Downloads/PS/SA_PS.pdf>.

* cited by examiner

PRIOR ART

PRESSURE-SENSING BLEED-BACK CONTROL VALVE WITH IMPROVED SEALING

This application is a continuation-in-part of, and claims the benefit of, U.S. utility patent application Ser. No. 15/782,664, filed Oct. 12, 2017, which itself claims the benefit of provisional U.S. Ser. No. 62/407,258, both of which are hereby incorporated by reference in their entireties.

I. BACKGROUND OF THE INVENTION

A. Field of Invention

The present invention generally relates to the field of bleed-back control valves, and real time in vivo fluid pressure measurements in medical catheterization procedures.

B. Description of the Related Art

Bleed-back control valves are well-known and have long been in use in surgical intervention and diagnostic procedures involving catheters. They are alternatively known as backflow control valves and hemostasis valves. One common bleed-back control valve is the Tuohy-Borst adapter, an example of which is shown in FIG. 1.

The Tuohy-Borst adapter is a very common tool in the medical profession even to the extent of being a standard; however, this tool has certain shortcomings. For instance, bleed-back can only be stopped when the microcatheter or guidewire 101 is locked in place with the cylindrical compression seal 102 closed. In FIG. 1, the compression seal 102 is shown in the open configuration, i.e. uncompressed. As the physician positions a prior art device 100, blood or other fluids will backflow to some extent. This creates a fluid spill, which is undesirable because it increases the risk of exposure to blood-borne pathogens. Generally, the physician will loosen the adapter just enough to allow the microcatheter or guidewire to slide. This tends to limit bleed-back, but it does not eliminate it.

Furthermore, Tuohy-Borst adapters have been used in connection with other hardware to make physiological fluid pressure measurements during endovascular procedures. For instance, catheter probes are known which are equipped with a pressure sensing transducer at the distal end, thus placing a pressure transducer at the site of a blockage (stenosis). More specifically, the transducer is used to measure pressure on the proximal and distal sides of the blockage. A pressure difference of more than 20 mmHg indicates treatment. In order to treat the blockage, the pressure sensing probe must be withdrawn, and a balloon angioplasty catheter must be inserted in its place, thus adding time and risk to the procedure. Alternatively, one could measure in vivo pressure by adding a second catheter, in a different artery. For instance, one catheter may be deployed to sense pressure, while a second catheter may be deployed to treat the blockage. Unfortunately, this entails adding significant cost to the procedure and risk to the patient.

Another known device for measuring pressures in vivo is a catheterization sheath with a pressure transducer disposed on the distal end of the sheath. One of the shortcomings of this device is that pressure can only be measured in one location. Moreover, sheaths come in relatively short, fixed lengths. Therefore, pressure can only be measured close to the puncture site. Moreover, sheaths also come in certain standard diameters, which may not be compatible with the blood vessels where a procedure is to be performed.

Other pressure measuring devices are known in this context, that can be used with the Tuohy-Borst adapter, which require fluidic equipment, and cannot provide a real time view of pressure. Known methods and devices require the physician to engage in tasks that interfere with the primary intervention procedure. It would be better to have a catheterization apparatus suitable for intervention which simultaneously senses pressure.

Some embodiments of the present invention may provide one or more benefits or advantages over the prior art.

II. SUMMARY OF THE INVENTION

Some embodiments may relate a pressure-sensing bleed-back control valve. The valve may include a main valve body defining a lumen extending from an access port at an upstream end to an opening at a downstream terminal end. The valve may further include an upstream main seal disposed in the lumen of the main valve body. Embodiments may further include a catheter fitting disposed at a downstream end of the main valve body, and a pressure transducer in fluid communication with the lumen of the main valve body.

Embodiments may also include a saline intake sidearm in fluid communication with the lumen of the main valve body.

Embodiments may also include an effluent sidearm in fluid communication with the lumen of the main valve body.

Embodiments may also include an effluent sidearm seal.

According to some embodiments the effluent sidearm seal is a stopcock.

According to some embodiments the lumen of the main valve body is divided into an upstream half and a downstream half, fluid communication between the upstream and downstream halves being blocked by the upstream main seal.

According to some embodiments the upstream main seal comprises a double cone seal.

According to some embodiments the upstream main seal comprises a compressible cylindrical seal having a through-hole fluidly communicative with the lumen of the main valve body, the through-hole being open when the compressible cylindrical seal is relaxed, and closed when a compressive axial force is applied to the compressible cylindrical seal.

According to some embodiments the cylindrical seal is received by a male threaded seat cooperating with a female threaded compression nut, the female threaded compression nut including an integral plunger to axially compress the compressible cylindrical seal.

According to some embodiments the catheter fitting is female a Luer nut freely rotatable about the main valve body.

Embodiments may relate to a pressure-sensing bleed-back control valve, comprising: a main valve body defining a lumen extending from an access port at an upstream end to an opening at a downstream terminal end; an upstream main seal disposed in the lumen of the main valve body; a catheter fitting disposed at a downstream end of the main valve body; a pressure transducer in fluid communication with the lumen of the main valve body; a saline intake sidearm in fluid communication with the lumen of the main valve body; an effluent sidearm in fluid communication with the lumen of the main valve body; and a stopcock in fluid communication with a lumen of the effluent sidearm.

According to some embodiments the lumen of the main valve body is divided into an upstream half and a downstream half, fluid communication between the upstream and downstream halves being blocked by the upstream main seal.

According to some embodiments the upstream main seal comprises a double cone seal.

According to some embodiments the upstream main seal comprises a compressible cylindrical seal having a through-hole fluidly communicative with the lumen of the main valve body, the through-hole being open when the compressible cylindrical seal is relaxed, and closed when a compressive axial force is applied to the compressible cylindrical seal.

According to some embodiments the cylindrical seal is received by a male threaded seat cooperating with a female threaded compression nut, the female threaded compression nut including an integral plunger to axially compress the compressible cylindrical seal.

According to some embodiments the catheter fitting is female a Luer nut freely rotatable about the main valve body.

Embodiments may relate to a method of measuring in vivo blood pressure comprising the steps of: feeding a catheter to a first location in a body of a patient without bleed-back; and collecting in vivo pressure data at the first location without locking a Tuohy-Borst fitting.

Embodiments may further include the steps of: feeding the catheter to a second location within the patient without bleed-back and without first unlocking the Tuohy-Borst fitting; and collecting in vivo pressure data at the second location without locking the Tuohy-Borst fitting.

Embodiments may also include the step of diagnosing a clot when the pressure at the first location is higher than the pressure at the second location by a predetermined amount.

Embodiments may also include the step of installing a balloon catheter without first removing an in vivo pressure microcatheter probe from the catheter.

Other benefits and advantages will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof, wherein like reference numerals indicate like structure, and wherein.

IV. DETAILED DESCRIPTION OF THE INVENTION

As used herein the terms "embodiment", "embodiments", "some embodiments", "other embodiments" and so on are not exclusive of one another. Except where there is an explicit statement to the contrary, all descriptions of the features and elements of the various embodiments disclosed herein may be combined in all operable combinations thereof.

Language used herein to describe process steps may include words such as "then" which suggest an order of operations; however, one skilled in the art will appreciate that the use of such terms is often a matter of convenience and does not necessarily limit the process being described to a particular order of steps.

Conjunctions and combinations of conjunctions (e.g. "and/or") are used herein when reciting elements and characteristics of embodiments; however, unless specifically stated to the contrary or required by context, "and", "or" and "and/or" are interchangeable and do not necessarily require every element of a list or only one element of a list to the exclusion of others.

The terms upstream and downstream are used herein to indicate the relative position or orientation of parts of an embodiment in an assembled state, and/or while in use. Their meaning will be clear in context to the ordinarily skilled artisan, but in general they refer to the direction of travel of a catheter as it is inserted into an embodiment, or fluid passing through the embodiment according to normal operation.

Figure 1:
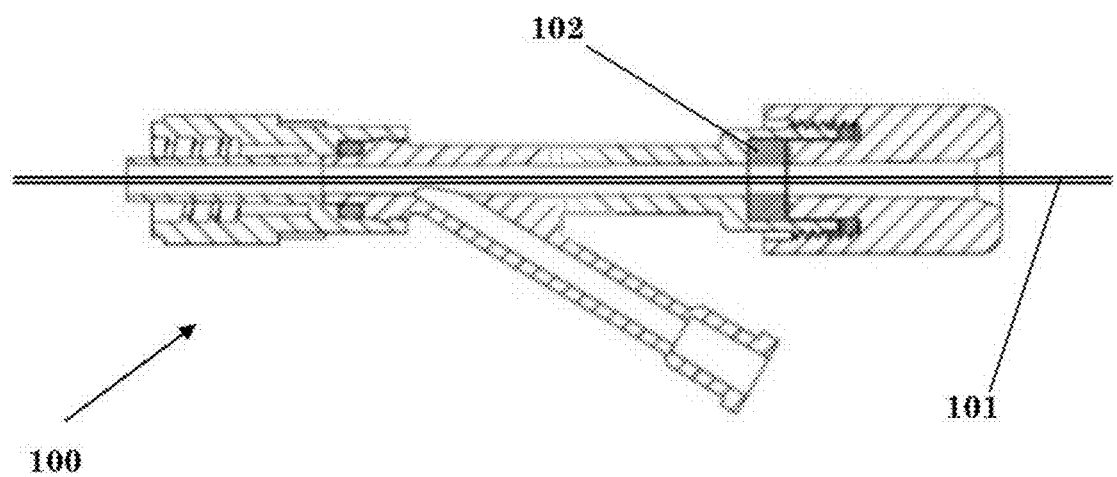
FIG. 1 illustrates a prior art device.
Figure 2:
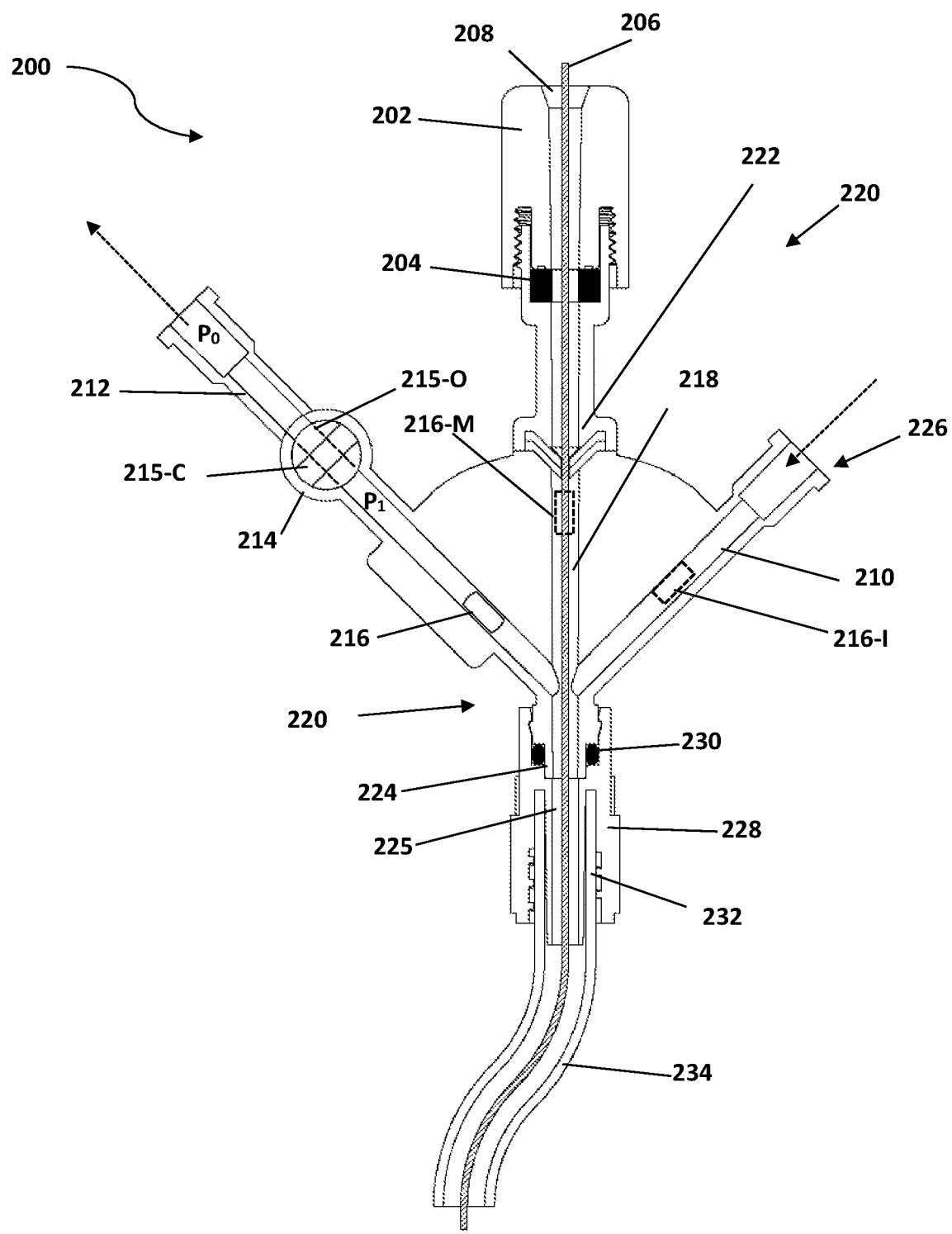
FIG. 2 is a cross sectional view of a two-sidearm embodiment with a catheter and guidewire installed.

Referring now to the drawings, wherein the showings are for purposes of illustrating embodiments of the invention only and not for purposes of limiting the same, FIG. 2 illustrates a Tuohy-Borst adapter 200 according to some embodiments of the invention. The adapter 200 includes a threaded fitting 202 containing a compressible cylindrical gasket 204. As the gasket 204 is axially compressed by the fitting applying a compressive axial force, it collapses around a microcatheter or guidewire 206 locking it in place and preventing blood or other fluids from backflowing through the access port 208. FIG. 2 further illustrates a saline intake sidearm 210 which may be in fluid communication, according to well-known means, with a saline source such as an IV bag or syringe (not shown). Saline may enter through the intake sidearm 210 and flow out through an effluent sidearm 212 provide the stopcock 214 is in an open position. As illustrated, stopcock 214 is closed. The closed position is indicated by valve port 215-C shown in unbroken lines, and the open position indicated by valve port 215-O shown in dashed lines. The skilled artisan will readily appreciate that a stopcock 214 is merely one of a wide variety of valve structures that can perform the required function of stopping fluid flow from the effluent sidearm 212. All such manual and automated valves, well-known in the art, are within the scope of the present invention to the extent that they perform the required function. Collectively, these structures are referred to herein as effluent sidearm seals. Notably, an effluent sidearm seal may be omitted from an embodiment provided that an external structure for stopping flow from the effluent sidearm is supplied to enable in vivo pressure measurements.

The access port 208 is illustrated herein as part of the threaded compression nut 202. However, access ports within the scope of the invention more broadly include any structure that performs the function of providing access to the lumen 218 of the main valve body 220 by microcatheters and/or guidewires. Furthermore, it is contemplated that embodiments may not necessarily include threaded compression nuts 202 as illustrated here, but may still provide such an access port. For instance, embodiments that omit the cylindrical compression seal 204 in favor of an alternative sealing and/or locking mechanism, as are well-known in the art, would not require a threaded compression nut.

A pressure transducer 216 is shown in the lumen of the effluent sidearm 212. The person having ordinary skill in the art will recognize that the pressure transducer 216 is advantageously disposed in a sidearm lumen. This may prevent the transducer 216, which may or may not be flush with the luminal wall, from interfering with the free movement of guidewires and/or microcatheters through the lumen 218 of the main valve body 220. However, embodiments may place the transducer 216 in the lumen of the main valve body 220 as indicated by 216-M, or in the intake sidearm 210 as indicated by 216-I. Both 216-M and 216-I are shown in dashed lines to indicate that these are alternative positions.

Moreover, the positioning of transducer 216 is not limited to the particular locations illustrated. More specifically, the skilled artisan will recognize that similar pressures will be read at any point in the volume bounded by the closed stopcock 214, 215-C the double cone seal 222, the terminal end 224 of the embodiment 200, and the terminal end 226 of the intake sidearm 210. Still further, while double cone seals 222 provide certain advantages, embodiments may or may not include double cone seals. Embodiments that omit double cone seals may place a pressure transducer 216 anywhere downstream of the cylindrical compression seal 204. The double cone seals 222 are more fully disclosed in U.S. patent application Ser. No. 15/782,664. In order for the embodiment to sense a physiological pressure of a patient the lumen 218 of the main valve body 220 must be closed to fluid flow upstream of the transducer 216. The cylindrical compression seal 204, double cone seals 222, or any of a wide variety of known fluid seals may be incorporated into an embodiment as a matter of design choice, as would be readily understood by the person having ordinary skill in the art. Collectively, these seals may be referred to as upstream main seals. As shown in FIG. 2, both the cylindrical seal and the double cone seal are in the lumen of the valve body in the sense that they are capable of occluding fluid flow therein.

With further regard to FIG. 2, the illustrated embodiment 200 includes a Luer lock nut 228 sealed to the main valve body 220 of the embodiment with an O-ring 230. The nut 228 is shown with a catheter 234 installed at the terminal end 224, the catheter having a male Luer connection 232. The catheter is in fluid communication with the lumen 218 of the main valve body through the opening 225 at the terminal end 224. The guidewire 206 is also shown extending through the embodiment 200 and coaxially into the catheter 234. The person having skill in the art will appreciate that a microcatheter (not shown) may be in place of the guidewire 206 without affecting pressure measurements.

Reference is made herein to Luer lock fittings. While common, the person having ordinary skill in the art will readily appreciate that this is merely one type of suitable fitting. Other well-known fittings may be selected by the ordinarily skilled artisan as a matter of design choice. Accordingly, the Luer nut may be more generally referred to as a "catheter fitting", which is contemplated to broadly encompass all known structures for performing the function of receiving a catheter.

Figure 3:
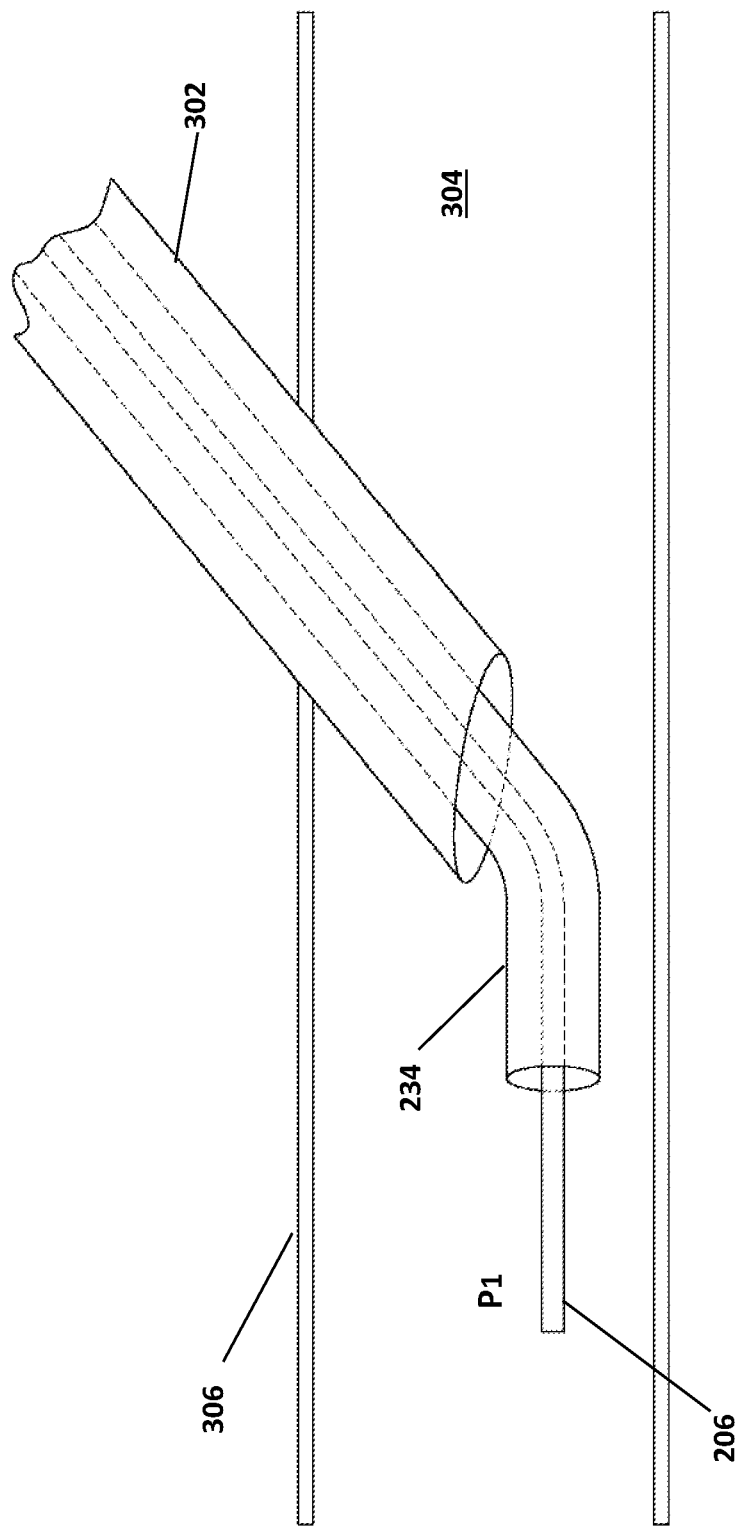
FIG. 3 is a view showing entry of an embodiment into a patient's blood vessel through a sheath.

Turning to FIG. 3, a catheter 234 is shown being fed into a blood vessel 306 of a patient through a sheath 302 as are commonly known in the art. FIG. 3 further illustrates the use of a guidewire 206 in positioning the catheter 234. The portion of the catheter 234 inside the sheath 302 is shown in broken lines, while the portion of the catheter 234 extending into the blood vessel lumen 304 is shown in solid lines. Likewise, the portion of the guidewire 206 that is inside the catheter 234 is shown in broken lines while the portion extending into the blood vessel lumen 304 is shown in solid lines. The pressure inside the blood vessel lumen 304 at the tip of the catheter is represented by $P_1$. This is the same pressure $P_1$ as shown in FIG. 2. Accordingly, the pressure at the tip of the catheter 234 is the same as the pressure measured by the transducer 216, provided stopcock 214 is closed.

Figure 4:
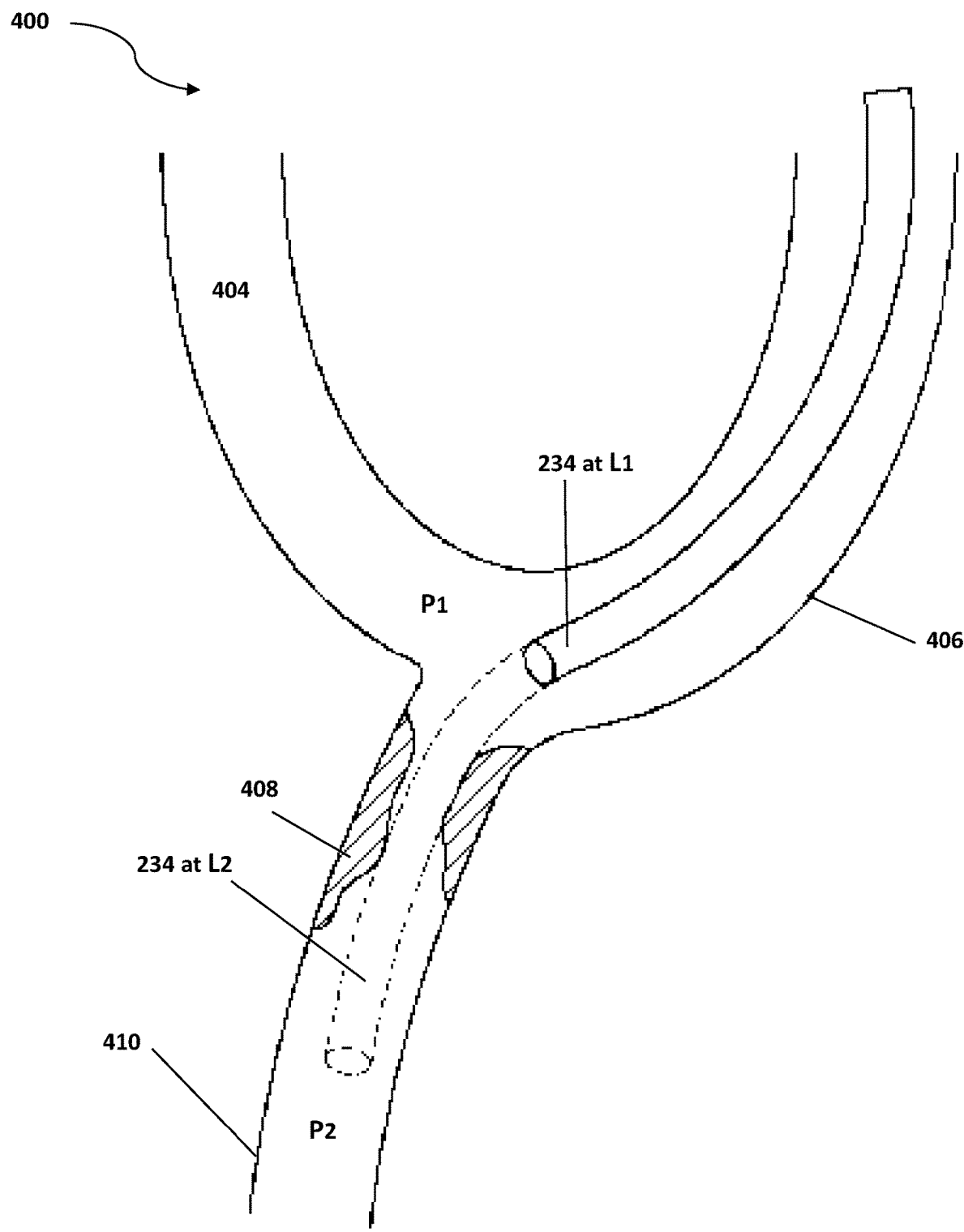
FIG. 4 is an illustration of a real time pressure measurement.

FIG. 4 illustrates real time pressure measurements 400 being taken at two different positions to detect a blockage. More specifically, the catheter 234 is shown at a first location L1, within the lumen 404 of a blood vessel 406, where a first pressure $P_1$ is measured. The vessel 406 is advantageously upstream of any potential blockage. The catheter 234 is then repositioned to location L2, which is advantageously downstream of a blockage 408 in blood vessel 410. The pressure at location L2 is indicated by $P_2$. The presence of blockage 408 is diagnosed when $P_2$ and $P_1$ differ by 20 mmHg or more. Referring back to FIG. 2, embodiments having the optional double cone seal 222 advantageously permit moving quickly from L1 to L2 without having to tighten and untighten nut 202 to stay the backflow of blood. Moreover, having diagnosed a blockage 408, the physician may proceed immediately to balloon angioplasty without having to change out a pressure probe catheter for a balloon catheter, or otherwise pause the intervention procedure.

With continued reference to FIG. 2, the person having ordinary skill in the art will recognize that one sidearm is sufficient for an embodiment, but having two sidearms has certain advantages. More specifically, having two sidearms permits a saline flush of the lumen 218 of the main valve body 220. This may be helpful to purge blood from the lumen 218 and/or to remove air bubbles. Furthermore, having two sidearms provides a readily available means for zeroing the pressure transducer 216. More specifically, when the stopcock 214 is in the opened position 215-O the transducer 216 feels pressure $P_0$. Thus, $P_0$ may be used as a zero-reference point, as it is expected to be close to atmospheric pressure. In contrast, when stopcock 214 is in the closed position 215-C the transducer 216 feels the pressure at the distal end of the catheter represented herein as $P_1$ and $P_2$ depending on context (see FIG. 4).

Importantly, the person having ordinary skill in the art will readily appreciate that the pressure felt by transducer 216 is an average of the pressure in vivo and the saline pressure. Furthermore, the skilled artisan will understand that common saline sources are typically at about 300 mmHg, and therefore must be modulated down to a pressure more closely approximating in vivo pressure. Generally, this is accomplished by decreasing saline flow rate to a low level on the order of a steady drip. This practice brings the pressure in the saline intake sidearm 210 close enough to the in vivo pressure for accurate pressure measurements to be made reliably. Generally, the saline source would be modulated down to just above in vivo pressure to prevent backflow.

Figure 5:
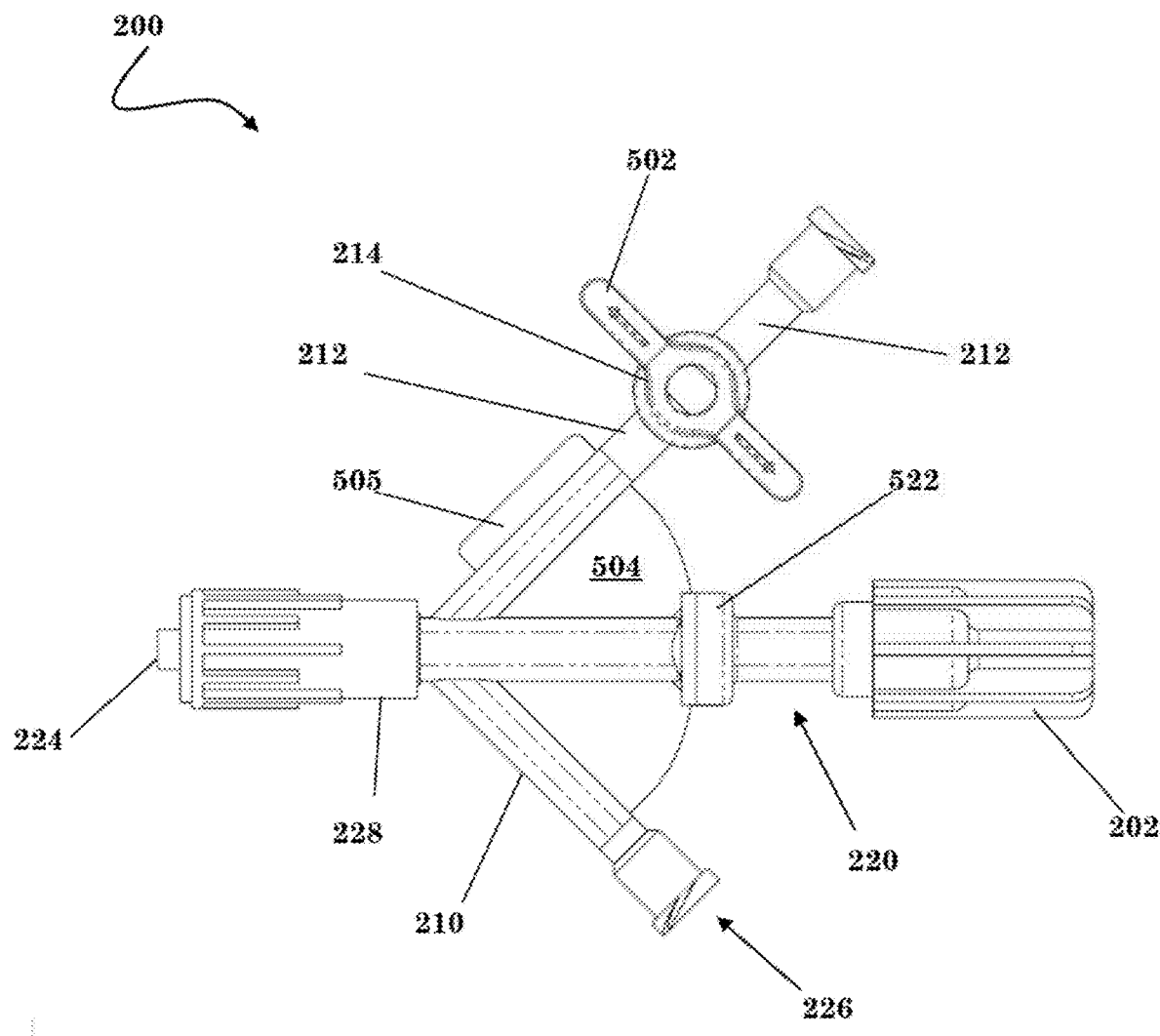
FIG. 5 is a top view of a two-sidearm embodiment.

Turning to FIG. 5, a top view of the two-sidearm embodiment 200 of FIG. 2 is shown. The threaded compression nut 202 is shown at the upstream end of the main valve body 220 and the Luer nut 228 is shown at the downstream end of the main valve body 220. The main valve body 220 is shown having an in-line housing 522 where the double cone seals 222 (see FIG. 2) are seated. The exterior of stopcock 214 is illustrated including knob 502. Finally, a stabilizing member 504 is shown connecting to the main valve body 220, effluent sidearm 212 and intake sidearm 210. The stabilizing member is advantageously provided for added strength to resist flexing and breakage. Moreover, the stabilizing member 504 provides structure to assist in holding the embodiment in place. The stabilizing member 504 may optionally extend slightly beyond one of the sidearms forming an overhang 505. This structure may be advantageous in some embodiments depending on the specific dimensions of the pressure transducer used, which will be a matter of design choice. In the illustrated embodiment, the lip 505 provides extra room for the transducer (not shown) to align with the lumen of the effluent sidearm 212.

Figure 6:
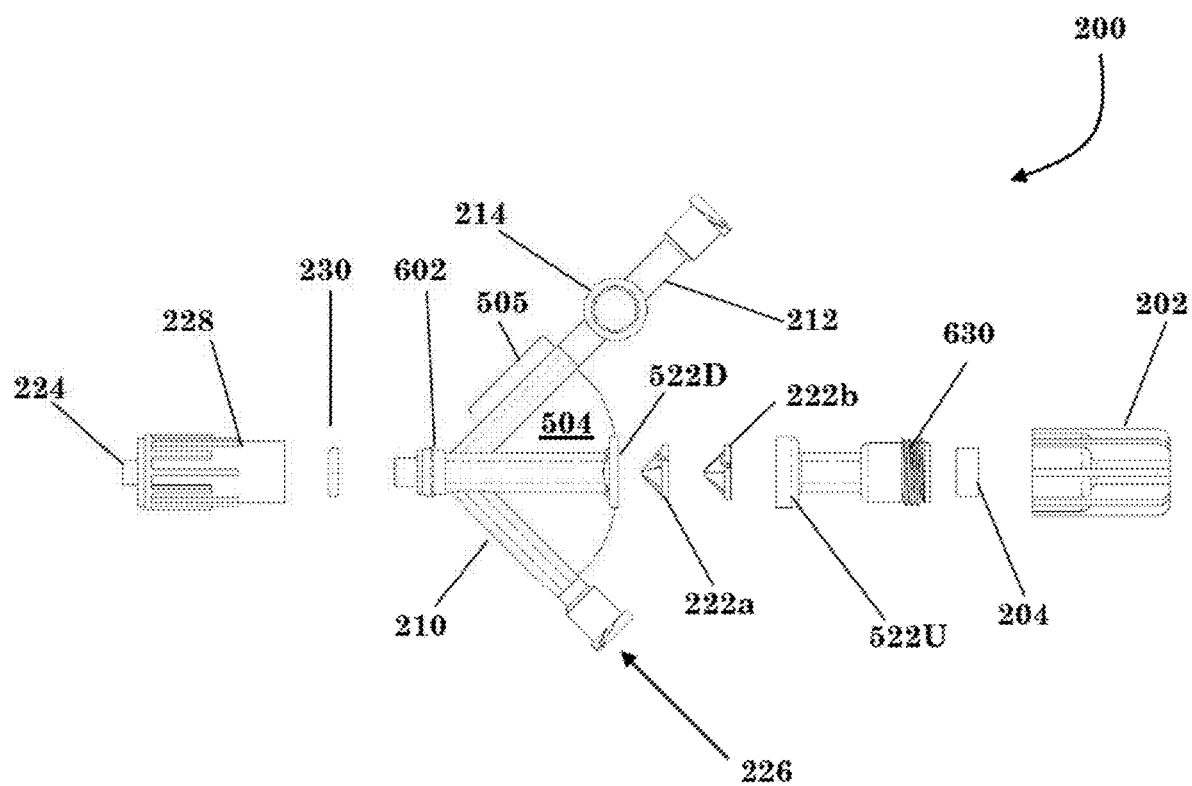
FIG. 6 is an exploded view of a two-sidearm embodiment.

Continuing to FIG. 6, the same embodiment 200 is shown in an exploded view. The compression nut 202 is shown in relation to a male threaded seat 630 which receives the cylindrical compression seal 204. The in-line housing 522 is shown comprising two parts, namely, and upstream half 522U and a downstream half 522D. The cone seals 222 are likewise shown separately as 222a and 222b. U.S. patent application Ser. No. 15/782,664 more fully discloses the structure, function, and orientation of these seals 222a, 222b. With continuing reference to FIG. 6, an annular ridge 602 is shown which fits into a complementary annular groove (not shown) located on an inside surface of the Luer nut 228. Its function is to rotatably retain the Luer nut 228 on the main valve body 220. The O-ring 230 seals the connection between the annular ridge 602 and groove (not shown) thus preventing leakage of liquids.

Figure 7:
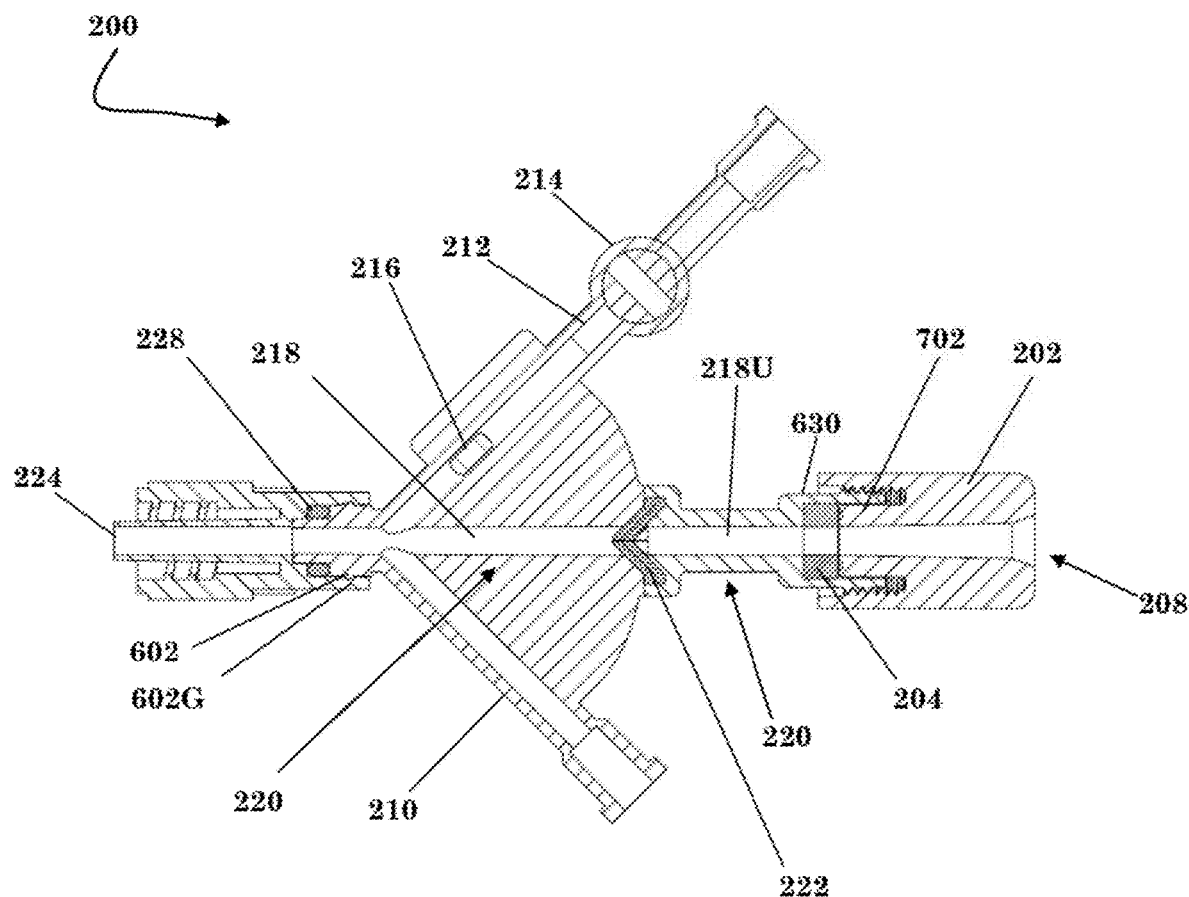
FIG. 7 is a cross sectional view of a two-sidearm embodiment.

FIG. 7 is a cross sectional view of embodiment 200 similar to that of FIG. 2. In contrast to FIG. 2, the embodiment 200 is illustrated without a catheter 234 or guidewire 206 installed. Thus, the double cone seals 222 are fully relaxed and in a closed position. Similarly, the cylindrical compression seal 204 is uncompressed, i.e. relaxed, thus leaving the upstream section of the lumen 218U of the main valve body 220 open. Additionally, the annular ridge 602 and complementary annular groove 602G are shown in union. Accordingly, the Luer nut 228 is free to rotate about the annular ridge 602. With further regard to FIG. 7, a compression seal 204 is received by a male threaded seat 630. The seal 204 is axially compressed by an integral plunger 702 member of the female threaded compression nut 202.

Figure 8:
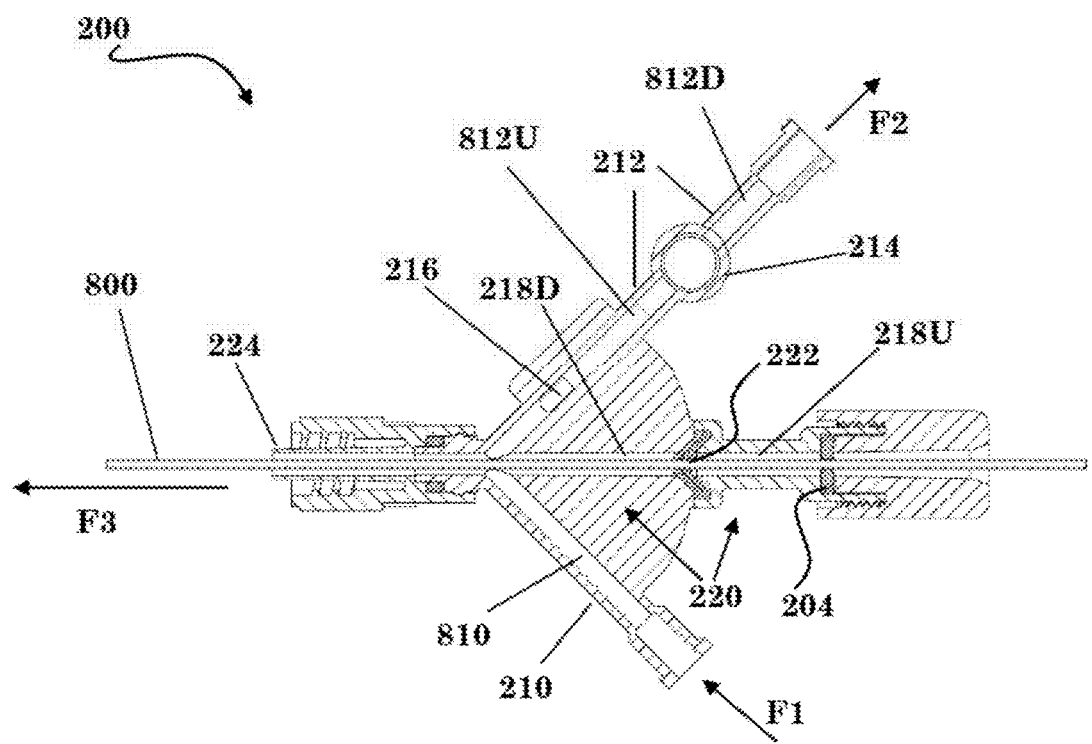
FIG. 8 is a cross sectional view showing a microcatheter cooperating with an embodiment.

Continuing to FIG. 8, the embodiment 200 is shown with a microcatheter 800 installed. In the illustrated configuration, the downstream terminal end 224 of the embodiment 200 is in fluid communication with the upstream lumen 812U of the effluent sidearm 212, including the pressure transducer 216. The terminal end 224 is also in fluid communication with the lumen 810 of the intake sidearm 210. Arrows F1, F2, and F3 show the usual direction of fluid flow through the embodiment 200 for the purpose of naming parts thereof "upstream" or "downstream". In the illustrated configuration, the terminal end is in fluid communication with the downstream lumen 812D of the effluent sidearm 212 when the stopcock 214 is open. In contrast, the upstream section of the lumen 218U of the main valve body 220 is in restricted fluid communication with the terminal end 224 because fluid is at least partially blocked by the double cone seals 222 whether or not they are receiving a microcatheter 800 or guidewire 206 (FIG. 2). Embodiments may either completely block fluid communication between the upstream lumen 218U of the main valve body 220 and the transducer 216, or they may partially block fluid communication. Either case is referred to herein as "restricted fluid communication". It is contemplated that embodiments having partially blocked fluid communication between the upstream lumen 218U and the transducer 216 provide sufficient fluid restriction to enable acceptable accuracy of in vivo continuous pressure measurements.

Figure 9:
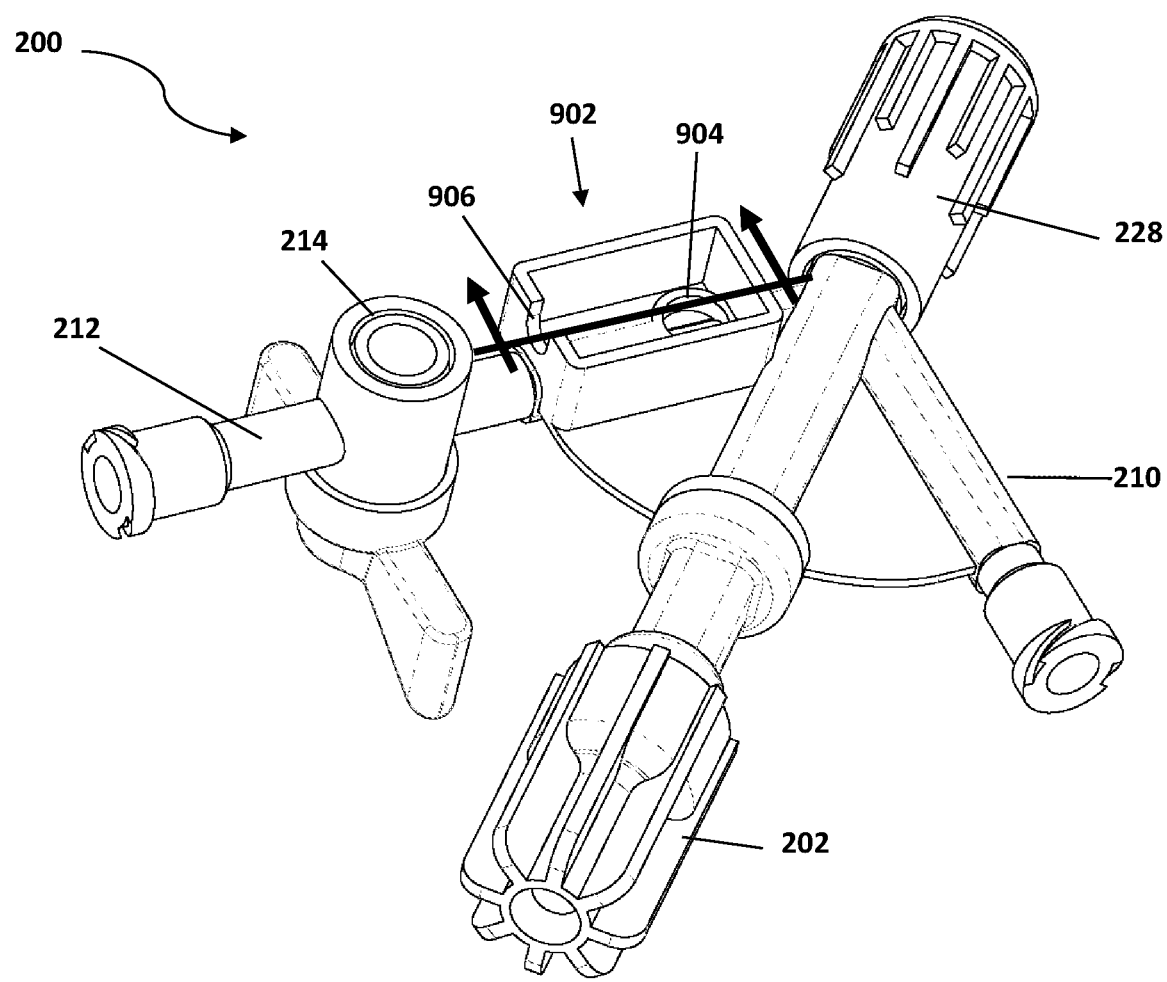
FIG. 9 is a bottom view of a two-sidearm embodiment.

FIG. 9 is a three-dimensional view of embodiment 200 as viewed from underneath. This figure shows the threaded compression nut 202 at the upstream end of the embodiment 200, the Luer nut 228 at the down stream end of the embodiment 200, and the intake 210 and effluent 212 sidearms. FIG. 9 also illustrates a housing 902 adapted to receive a pressure transducer 216 (not shown). A pressure sensitive member of the pressure transducer 216 (not shown) would be in fluid communication with the lumen of the effluent sidearm 212 through aperture 904. Advantageously, any of a wide variety of known structures may be optionally incorporated into an embodiment to provide a liquid-tight seal between the transducer and the aperture 904.

Continuing in reference to FIG. 9, an opening 906 is also provided in a sidewall of the housing 902 to receive a wire (not shown) enabling data communication between the pressure transducer and an external device such as a microcomputer or signal processing electronics. The person having ordinary skill in the art will appreciate that the precise dimension of the housing 902 are not important, and would depend on the particular transducer selected as a matter of design choice. Further, the opening 906 may take on many alternative forms or omitted entirely. More specifically, the skilled artisan would be aware of numerous well-known structures capable of similarly allowing for a wired connection to external electronics, all of which are within the scope of the invention. Further, embodiments of the invention can alternatively comprise wireless telemetry thereby obviating the need to accommodate wires.

Figure 10:
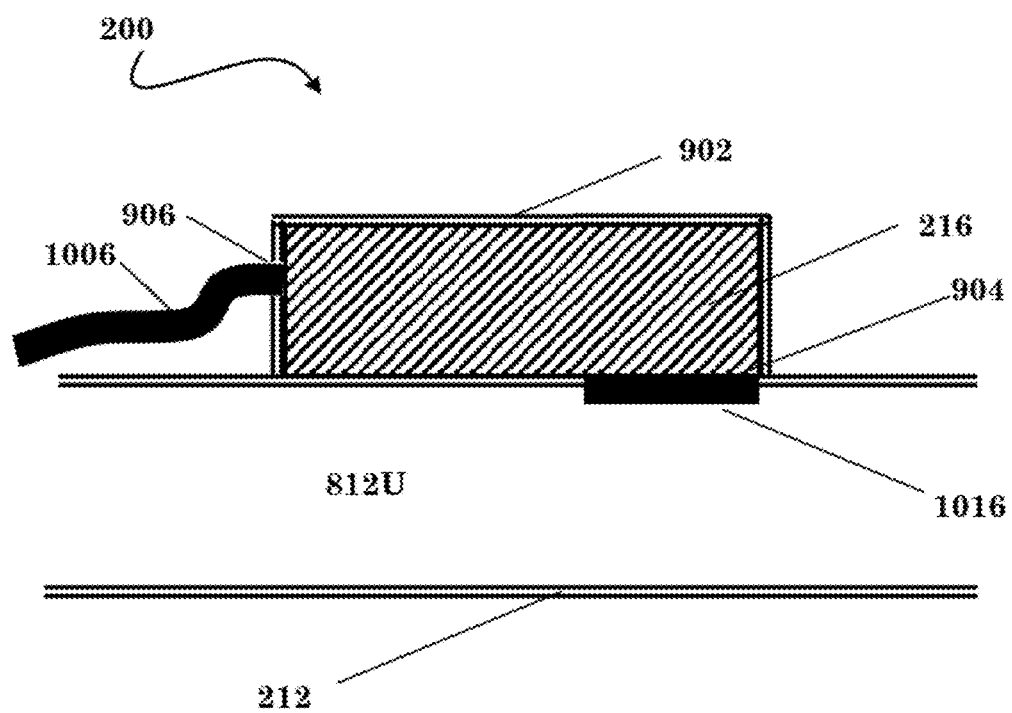
FIG. 10 is a cross sectional view taken along line A-A of FIG. 9 showing the pressure transducer in relation to the sidearm lumen.

FIG. 10 illustrates one way in which an embodiment may incorporate a pressure transducer. Particularly, a cross sectional view of the embodiment 200 of FIG. 9 is shown. The cross section is taken along line A-A of FIG. 9. A pressure transducer module 216 is shown enclosed in housing 902. A pressure sensitive member 1016 of the transducer 216 protrudes through aperture 904 into the upstream lumen 812U of the effluent sidearm 212. A wire 1006 is also shown protruding through opening 906 of the housing 902. Though not shown, the wire 1006 terminates out of view connecting to external electronics. The person having ordinary skill in the art would readily appreciate that there are numerous equivalent structural arrangements to accomplish the same pressure transduction function, all of which are contemplated to be within the scope of the present invention.

Figure 11:
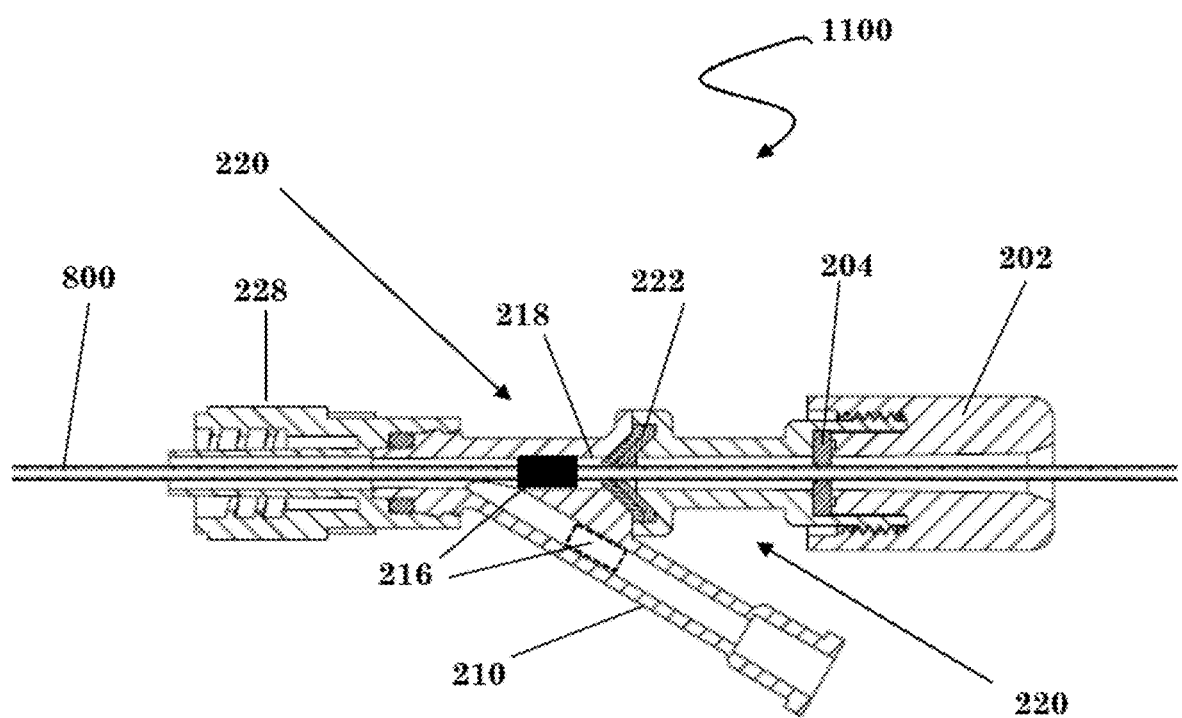
FIG. 11 is a view of a one-sidearm embodiment cooperating with a microcatheter.

FIG. 11 illustrates an embodiment 1100 having one rather than two sidearms; however, the skilled artisan will appreciate that even this sidearm may be eliminated while maintaining the invention's pressure sensing capability. The illustrated embodiment is otherwise structurally very similar to that which is shown in FIG. 2, the primary difference being that the effluent sidearm 212 is omitted from embodiment 1100. Embodiment 1100 thus includes a threaded compression nut 202, suitably adapted to compress cylindrical seal 204 so as to lock a microcatheter 800 or guidewire (not shown) in place. The embodiment also includes double cone seals 222 allowing repositioning of a microcatheter 800 without bleed-back. Although the illustrated embodiment 1100 includes a double cone seal 222, similar to embodiment 200, this feature is optional. The pressure sensing features of the embodiment would not be impaired by leaving out this structure. Embodiment 1100 also includes a Luer nut 228 for attaching a catheter (not shown).

A saline intake sidearm 210 is also provided; however, in embodiment 1100 the only path for saline is through the downstream section of the main valve body's 220 lumen 218. A pressure transducer 216 is shown in solid black in the lumen 218 downstream of the double cone seal 222. Similar to embodiment 200, this is only one of a variety of possible positions. To illustrate, an alternative location for the transducer 216 is shown in dashed lines in the intake sidearm 210. The saline intake sidearm 210 may be used to zero the pressure transducer 216. For instance, a stopcock (not shown) may be installed on the sidearm 210 to allow the lumen 218 to equalize with atmospheric pressure.

Zero-sidearm embodiments are very similar in structure to 1100 except that sidearm 210 would be omitted. Such embodiments may zero the pressure transducer 216 by loosening nut 202 to allow the cylindrical seal 204 to relax enough to permit an arbitrary tool, as would be apparent to the skilled artisan, to be inserted into the lumen 218 opening the double cone seals 222. For instance, a suitable tool may be a hollow cylinder that coaxially slides over the microcatheter 800 and impinges upon the seals 222 thus lifting them off of the microcatheter and opening the fluid path between the transducer 216 and the external atmosphere.

It will be apparent to those skilled in the art that the above methods and apparatuses may be changed or modified without departing from the general scope of the invention. The invention is intended to include all such modifications and alterations insofar as they come within the scope of the appended claims or the equivalents thereof.

Having thus described the invention, it is now claimed:

I claim:

1. A pressure-sensing bleed-back control valve, comprising:
   a main valve body defining a lumen extending from an access port at an upstream end to an opening at a downstream terminal end;
   an upstream main seal disposed in the lumen of the main valve body;
   a catheter fitting disposed at a downstream end of the main valve body; and
   a pressure transducer in fluid communication with the lumen of the main valve body, wherein the pressure transducer is disposed in the lumen of the main valve body or any sidearm thereof.

2. The valve of claim 1, wherein the any sidearm further comprises a saline intake sidearm in fluid communication with the lumen of the main valve body.

3. The valve of claim 2, wherein the any sidearm further comprises an effluent sidearm in fluid communication with the lumen of the main valve body.

4. The valve of claim 3, further comprising an effluent sidearm seal.

5. The valve of claim 4, wherein the pressure transducer is disposed in a lumen of the effluent sidearm upstream of the effluent sidearm seal.

6. The valve of claim 2, wherein the lumen of the main valve body is divided into an upstream half and a downstream half, fluid communication between the upstream and downstream halves being blocked by the upstream main seal.

7. The valve of claim 6, wherein the upstream main seal comprises a double cone seal.

8. The valve of claim 2, wherein the upstream main seal comprises a compressible cylindrical seal having a through-hole fluidly communicative with the lumen of the main valve body, the through-hole being open when the compressible cylindrical seal is relaxed, and closed when a compressive axial force is applied to the compressible cylindrical seal.

9. The valve of claim 8, wherein the compressible cylindrical seal is received by a male threaded seat cooperating with a female threaded compression nut, the female threaded compression nut including an integral plunger to axially compress the compressible cylindrical seal.

10. The valve of claim 2, wherein the catheter fitting is a female Luer nut freely rotatable about the main valve body.

11. A pressure-sensing bleed-back control valve, comprising:
    a main valve body defining a lumen extending from an access port at an upstream end to an opening at a downstream terminal end;
    an upstream main seal disposed in the lumen of the main valve body;
    a catheter fitting disposed at a downstream end of the main valve body;
    a saline intake sidearm in fluid communication with the lumen of the main valve body;
    an effluent sidearm in fluid communication with the lumen of the main valve body;
    an effluent sidearm seal in fluid communication with a lumen of the effluent sidearm; and
    a pressure transducer in fluid communication with the lumen of the main valve body, wherein the pressure transducer is disposed in the lumen of the main valve body, the saline intake sidearm, or the effluent sidearm.

12. The valve of claim 11, wherein the lumen of the main valve body is divided into an upstream half and a downstream half, fluid communication between the upstream and downstream halves being blocked by the upstream main seal.

13. The valve of claim 12, wherein the upstream main seal comprises a double cone seal.

14. The valve of claim 11, wherein the upstream main seal comprises a compressible cylindrical seal having a through-hole fluidly communicative with the lumen of the main valve body, the through-hole being open when the compressible cylindrical seal is relaxed, and closed when a compressive axial force is applied to the compressible cylindrical seal.

15. The valve of claim 14, wherein the cylindrical seal is received by a male threaded seat cooperating with a female threaded compression nut, the female threaded compression nut including an integral plunger to axially compress the compressible cylindrical seal.

16. A method of measuring in vivo blood pressure comprising the steps of:
    providing a pressure-sensing bleed-back control valve according to claim 11;
    installing a catheter in the pressure-sensing bleed-back control valve;
    providing a saline flow through the saline intake sidearm of the bleed-back control valve;
    inserting the catheter into a blood vessel of a patient;
    opening the effluent sidearm seal of the pressure-sensing bleed-back control valve to atmospheric pressure; and
    recording a zero pressure while the effluent sidearm seal is open.

17. The method of claim 16, further comprising the steps of:

feeding the catheter to a first location in a body of the patient without bleed-back; and collecting in vivo pressure data at the first location without locking a Tuohy-Borst fitting.

18. The method of claim 17, further comprising the steps of:

feeding the catheter to a second location within the patient without bleed-back and without first unlocking the Tuohy-Borst fitting; and collecting in vivo pressure data at the second location without locking the Tuohy-Borst fitting.

19. The method of claim 18, further comprising the step of diagnosing a clot when the pressure at the first location is higher than the pressure at the second location by a predetermined amount.

20. The method of claim 19, further comprising the step of installing a balloon catheter without first removing an in vivo pressure microcatheter probe from the catheter.

\* \* \* \* \*